(12) United States Patent
Bugamelli et al.

(10) Patent No.: US 10,737,052 B2
(45) Date of Patent: Aug. 11, 2020

(54) FLUID COUPLING MEMBER INCLUDING VALVE MEMBER

(71) Applicant: KONINKLIJKE PHILIPS N.V., Eindhoven (NL)

(72) Inventors: Antonio Bugamelli, Mars, PA (US); Richard Thomas Haibach, Verona, PA (US); Lauren Patricia Chodkowski, Pittsburgh, PA (US); Marcel Douglas Jaffre, Wendel, PA (US); Joseph Takahashi, Pittsburgh, PA (US); Stephen P. Turcsanyi, N. Huntington, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1218 days.

(21) Appl. No.: 14/911,554

(22) PCT Filed: Aug. 12, 2014

(86) PCT No.: PCT/IB2014/063863
§ 371 (c)(1),
(2) Date: Feb. 11, 2016

(87) PCT Pub. No.: WO2015/022629
PCT Pub. Date: Feb. 19, 2015

(65) Prior Publication Data
US 2016/0184549 A1    Jun. 30, 2016

Related U.S. Application Data

(60) Provisional application No. 61/864,873, filed on Aug. 12, 2013.

(51) Int. Cl.
*A61M 16/20* (2006.01)
*A61M 16/08* (2006.01)
(Continued)

(52) U.S. Cl.
CPC .......... *A61M 16/208* (2013.01); *A61M 16/06* (2013.01); *A61M 16/0816* (2013.01); *F16K 15/031* (2013.01)

(58) Field of Classification Search
CPC ................ A61M 16/208; A61M 16/06; A61M 16/0816; F16K 15/031
See application file for complete search history.

(56) References Cited

U.S. PATENT DOCUMENTS 1,373,686 A    4/1921  Townsend
3,814,124 A *  6/1974  Bell ...................... F16K 15/031
                                                137/454.2
(Continued)

FOREIGN PATENT DOCUMENTS

CN    101765443 A    6/2010
CN    102245251 A    11/2011
(Continued)

*Primary Examiner* — Timothy A Stanis
*Assistant Examiner* — Jonathan S Paciorek
(74) *Attorney, Agent, or Firm* — Michael W. Haas

(57) ABSTRACT

A fluid coupling member includes a housing having an interior and an exterior, the interior of the housing defining an airflow path through the fluid coupling member, a valve member pivotally attached to the interior of the housing, and at least one protrusion formed on the valve member or the housing. The at least one protrusion is structured to prevent the valve member from becoming stuck in a downward folded position against the housing.

13 Claims, 9 Drawing Sheets

(51) Int. Cl.
 *F16K 15/03* (2006.01)
 *A61M 16/06* (2006.01)

(56) References Cited

U.S. PATENT DOCUMENTS

| | | | | |
|---|---|---|---|---|
| 5,123,685 | A * | 6/1992 | Donovan | E05C 17/04 |
| | | | | 16/82 |
| 6,050,294 | A * | 4/2000 | Makowan | E03B 7/077 |
| | | | | 137/527 |
| 7,021,314 | B1 * | 4/2006 | Lane | A61F 2/203 |
| | | | | 128/200.26 |
| 7,152,603 | B1 * | 12/2006 | Crump | A61M 16/0463 |
| | | | | 128/207.14 |
| 8,365,731 | B2 | 2/2013 | Ho | |
| 9,174,018 | B2 | 11/2015 | Ho | |
| 2007/0295338 | A1 * | 12/2007 | Loomas | A61M 15/08 |
| | | | | 128/207.18 |
| 2009/0065729 | A1 * | 3/2009 | Worboys | A61M 16/06 |
| | | | | 251/367 |
| 2010/0236549 | A1 * | 9/2010 | Selvarajan | A61M 16/06 |
| | | | | 128/202.22 |
| 2011/0265796 | A1 | 11/2011 | Amarasinghe | |
| 2015/0114504 | A1 | 4/2015 | Berkeley et al. | |
| 2018/0328507 | A1 * | 11/2018 | Balcarczyk | F16K 17/164 |

FOREIGN PATENT DOCUMENTS

| | | |
|---|---|---|
| GB | 1373686 | 11/1974 |
| GB | 2473826 A2 | 3/2011 |
| JP | 2002285964 A | 10/2002 |
| WO | WO0038772 A1 | 7/2000 |
| WO | WO2013006899 A1 | 1/2013 |

\* cited by examiner

FLUID COUPLING MEMBER INCLUDING VALVE MEMBER

CROSS-REFERENCE TO RELATED APPLICATIONS

This patent application claims the priority benefit under 35 U.S.C. § 371 of international patent application no. PCT/IB2014/063863, filed Aug. 12, 2014, which claims the priority benefit under 35 U.S.C. § 119(e) of U.S. Provisional Application No. 61/864,873 filed on Aug. 12, 2013, the contents of which are herein incorporated by reference.

BACKGROUND OF THE INVENTION

1. Field of the Invention

The present invention pertains to a fluid coupling member including a valve member used to control the flow of a fluid, such as, without limitation, a flow of breathing gas in a patient interface device, and, in one or more particular embodiments, to an anti-asphyxia valve for use in a patient interface device structured to deliver a flow of breathing gas to a patient to treat a sleep disorder breathing condition such as obstructive sleep apnea (OSA).

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Anti-asphyxia features (AAF) used in conjunction with OSA therapy are required as a safety device in all masks that cover the nose and mouth. During respiratory therapy, should pressure no longer become available due to a power outage or a pump failure in the ventilator or pressure support device, the patient will continue to be able to breathe with the use of an AAF.

One typical AAF device configuration employs a flap style valve typically positioned within the fluid coupling conduit (e.g. elbow connector) of the mask. Such a flap style valve is fundamentally a reed style check valve. As the pressure from the ventilator or pressure support device is applied, the flap style valve opens, allowing air flow to the patient. When no pressure comes from the ventilator or pressure support device, the flap seats on a shelf disposed in the fluid coupling conduit and allows exhalation and inhalation at atmospheric pressure through a hole to atmosphere. The flap also serves to prevent the patient from pulling air from the volume of air in the gas delivery tubes and the ventilator or pressure support device.

A current development trends within the design of masks for non-invasive ventilation and pressure support therapies is impacting the required functionally of supporting components, such as AAF devices, used therewith. This trend is the implementation of smaller gas delivery tubing (e.g., 15 mm inside diameter). These features require a balancing of the necessary effective flow area to limit the pressure drop across the AAF while maintaining a smaller package profile. Achieving such balancing has proven to be challenging in connection with AAFs having the prior art configuration described above. For example, the shelf on which the flap style valve rests in the prior art configuration described above blocks part of the airflow to the patient.

SUMMARY OF THE INVENTION

Accordingly, it is an object of the present invention to provide a fluid coupling member including a valve member that overcomes the shortcomings of conventional configurations used in, for example, patient interface devices structured to deliver a flow of breathing gas to a user. This object is achieved according to one embodiment of the present invention by providing a fluid coupling member including a valve member that removes the need for a shelf and increases the effective flow area while maintaining a smaller package profile.

It is yet another object of the present invention to prevent the valve member from becoming stuck in a downward folded position.

In one embodiment, a fluid coupling member is provided that includes a housing having an interior and an exterior, the interior of the housing defining an airflow path through the fluid coupling member, a valve member being pivotally attached to the interior of the housing, and at least one protrusion formed on the valve member or the housing. At least one of the protrusions is structured to prevent the valve member from becoming stuck in a downward folded position against the housing.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
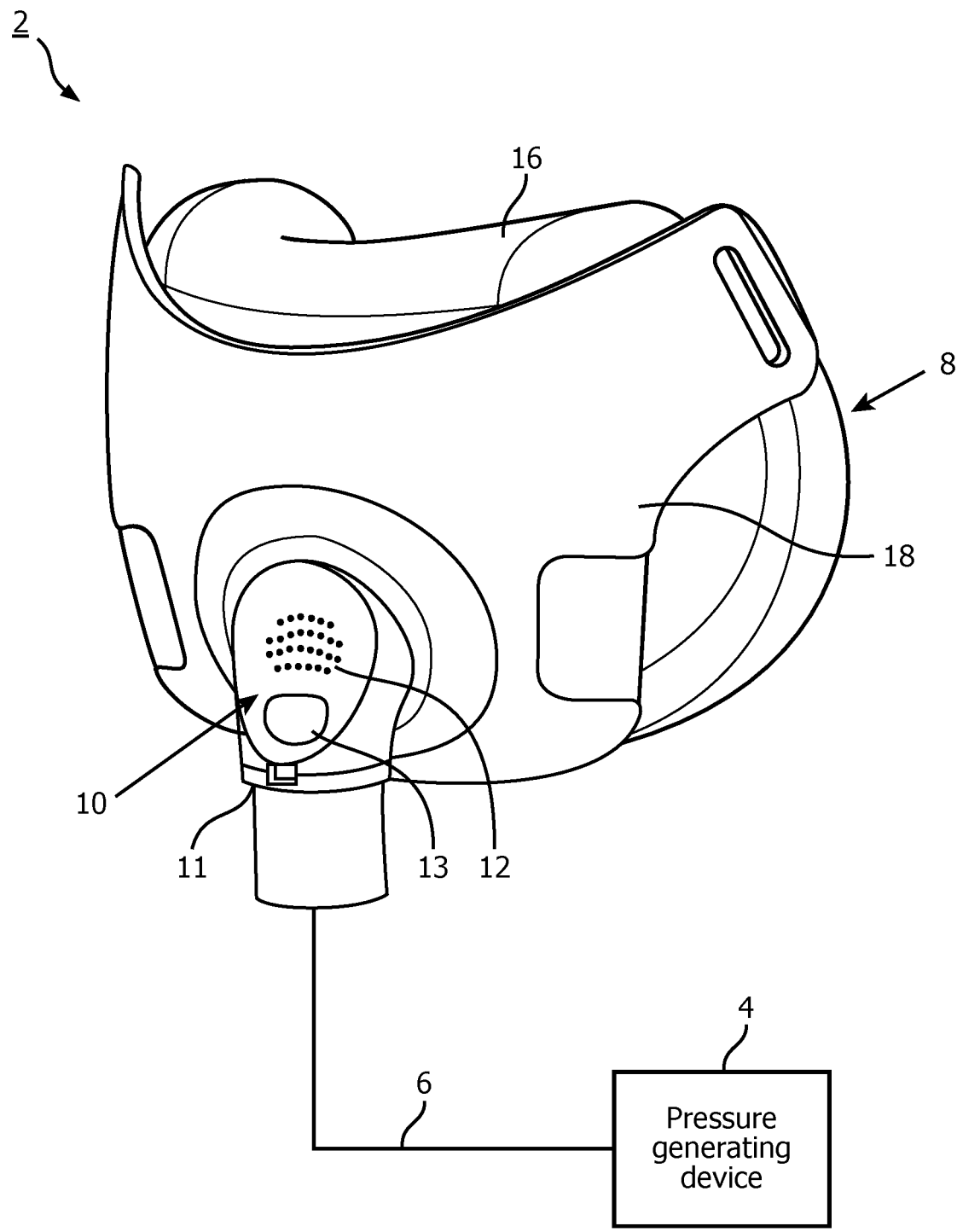
FIG. 1 is a schematic diagram of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the disclosed concept is generally shown in FIG. 1. System 2 includes a pressure generating device 4, a delivery conduit 6, and a patient interface device 8 including an elbow connector 10 fluidly coupled to delivery conduit 6. Elbow connector 10 includes a housing 11 which defines the exterior shape and interior airflow path of elbow connector 10. Exhalation holes 12 and an atmospheric port 13 are formed in housing 11. Elbow connector 10 further includes a valve member 14 (see, e.g., FIG. 2) disposed within elbow connector 10 and pivotally attached to the housing 11.

Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the illustrated embodiment, patient interface 8 is a nasal/oral mask structured to cover the nose and mouth of the patient. However, any type of patient interface device 8, such as, without limitation, a nasal mask that covers the patient's nose, a nasal cushion having nasal prongs that are received within the patient's nares, or a full face mask that covers the patient's face, which facilitates the delivery of the flow of breathing gas to, and the removal of a flow of exhalation gas from, the airway of a patient may be used while remaining within the scope of the present disclosed concept. In the embodiment shown in FIG. 1, patient interface device 8 includes a flexible cushion 16 and a rigid or semi-rigid shell 18. Straps (not shown) of a headgear component may be attached to shell 18 to secure patient interface device 8 to the patient's head. An opening in shell 18 to which elbow connector 10 is coupled allows the flow of breathing gas from pressure generating device 4 to be communicated to an interior space defined by shell 18 and cushion 16, and then, to the airway of a patient.

Figure 2:
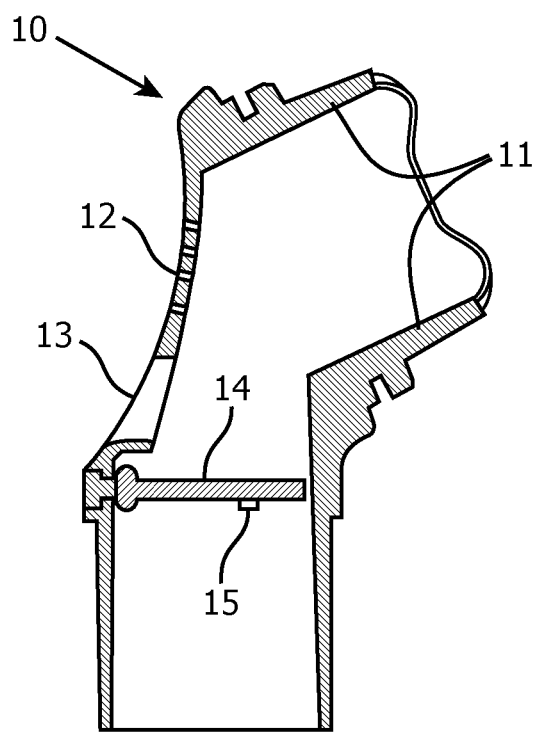
FIG. 2 is an side cross-sectional view and FIGS. 3 and 4 are bottom cross-sectional views of an elbow connector according to one exemplary embodiment of the invention.
Figure 3:
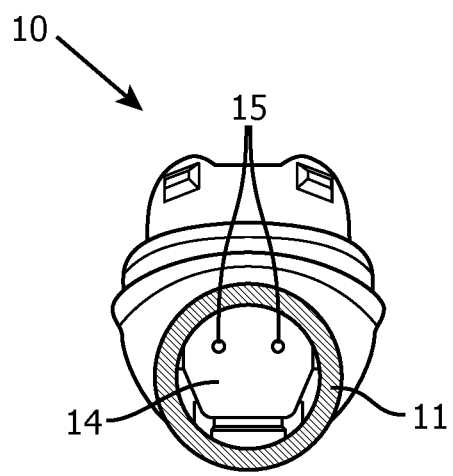
Figure 4:
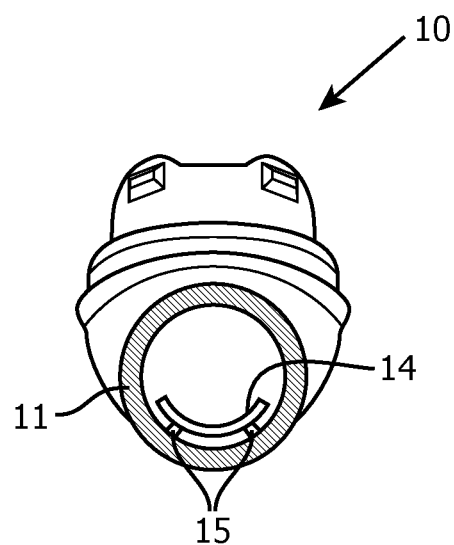

FIGS. 2-4 illustrate elbow connector 10 in accordance with one exemplary embodiment of the disclosed concept. FIG. 2 is a side cross-sectional view of elbow connector 10. FIG. 3 is a bottom cross-sectional view of elbow connector 10 when valve member 14 is in an unfolded position (also referred to as a "neutral position") and FIG. 4 is a bottom cross-sectional view of elbow connector 10 when valve member 14 is a downward folded position. The unfolded position refers to the position valve member 14 is in when neither gas from pressure generating device 4 or the patient's breath provide enough pressure to fold valve member 14 up or down. When gas from pressure generating device 4 does not apply pressure to valve member 14, but gas from the patient's breath does provide pressure to valve member 14, valve member 14 may fold down as shown in FIG. 4.

In the exemplary embodiment, valve member 14 is made of an elastomeric material, such as, without limitation, silicone, urethane, natural rubber, latex, and/or fabrics having a durometer between 20 and 70 shore A.

Valve member 14 includes protrusions on its bottom side. In one exemplary embodiment shown in FIGS. 2-4, the protrusions are a pair of posts 15. When valve member 14 is folded down, as shown in FIG. 4, posts 15 abut against the interior surface of housing 11. Under normal operation, valve member 14 should transition from downward folded position to the unfolded position, as shown in FIG. 2, when pressure from the patient's breath is removed, and should transition to an upward folded position when pressure is supplied from pressure generating device 4. However, if posts 15 were not present and valve member 14 were permitted to directly abut against housing 11, valve member 14 could become stuck in the downward folded position. For example, if valve member 14 directly abutted against and conformed to the shape of the interior surface of housing 11, valve member 14 might remain folded down even when pressure from the patient's breath is removed or when pressure is applied by gas from pressure generating device 4. When protrusions such as posts 15 are present, valve member 14 can more easily transition from the downward folded position to the unfolded or upward folded positions.

In the exemplary embodiment of FIGS. 2-4, posts 15 each have a length equal to or greater than 1 mm. However, the disclosed concept is not limited thereto. It is contemplated that any suitable length may be selected for posts 15 without departing from the scope of the disclosed concept. It is also contemplated that the length of the posts 15 may be selected in consideration of the diameter of the interior of housing 11. In some exemplary embodiments the ratio of the interior diameter of housing 11 to the length of the posts 15 is within a range of about 5.5-9.5.

While protrusions are a pair of posts 15 on the bottom side of valve member 14 in the exemplary embodiment shown in FIGS. 2-4, it is contemplated that the number, size and/or shape of the posts 15 can vary without departing from the scope of the disclosed concept. It is also contemplated that a textured pattern on the bottom side of valve member 14 may be employed instead of posts 15 without departing from the scope of the disclosed concept. It is also contemplated that valve member 14 and/or the interior surface of housing 11 may be coated with a non-stick material such as Teflon to assist in preventing valve member 14 from becoming stuck in the folded down position. It is also contemplated that the protrusions may take forms other than posts 15, as will be described herein with reference to FIGS. 5-7.

Figure 5:
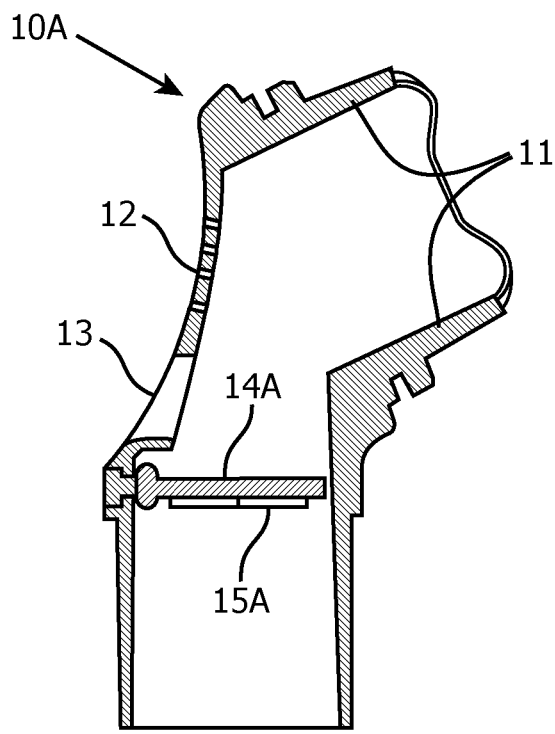
FIG. 5 is an side cross-sectional view and FIGS. 6 and 7 are bottom cross-sectional views of an elbow connector according to another exemplary embodiment of the invention.
Figure 6:
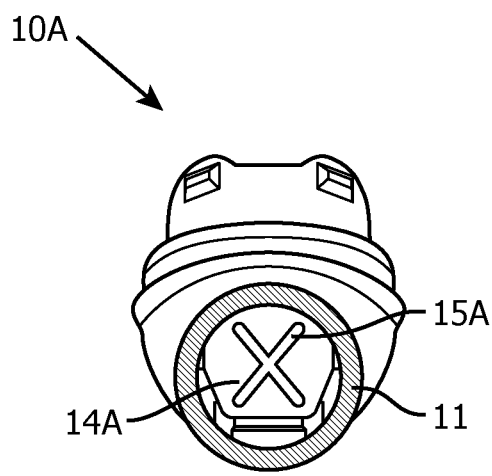
Figure 7:
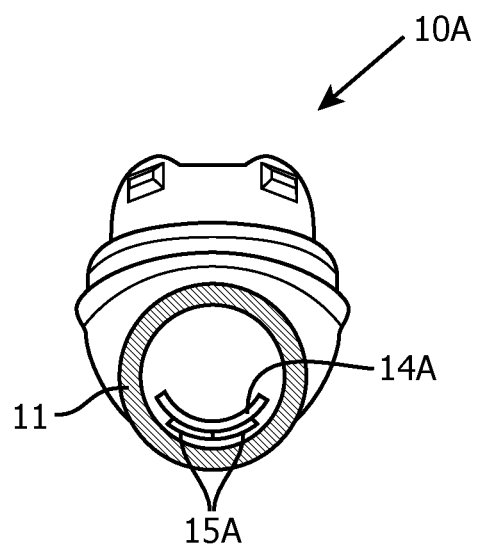

FIGS. 5-7 illustrate an elbow connector 10A including a valve member 14A having ridges 15A formed on its bottom side in accordance with another exemplary embodiment of the disclosed concept. FIG. 5 is a side cross-sectional view of elbow connector 10A. FIG. 6 is a bottom cross-sectional view of elbow connector 10A when valve member 14A is in an unfolded position and FIG. 7 is a bottom cross-sectional view of elbow connector 10A when valve member 14A is folded down.

Elbow connector 10A is similar to elbow connector 10. However, the protrusions on valve member 14A of elbow connector 10A are ridges 15A rather than posts 15. When valve member 14A is folded down, as shown in FIG. 7, ridges 15A abut against the interior surface of housing 11 and help to prevent valve member 14A from becoming stuck in the folded down position. In addition to abutting against the interior surface of housing 11, ridges 15A also provide structural support for valve member 14A which can further aid in preventing valve member 14A from becoming stuck in the folded down position. In more detail, when valve member 14A is formed of a relatively flexible material such as, for example, silicone, valve member 14A can become susceptible to conforming to the interior shape of housing 11 and becoming stuck in the folded down position. Structural support provided by ridges 15A further helps to prevent valve member 14A from becoming stuck in this manner.

In the exemplary embodiment shown in FIGS. 5-7, ridges 15A form a crossing pattern. However, it is contemplated that ridges 15A may take any suitable form without departing from the scope of the disclosed concept. Although ridges 15A are formed on the bottom side of valve member 14A, it is also contemplated that one or more ridges may be formed on the top side of a valve member, as will be described in more detail with reference to FIGS. 8-10.

Figure 8:
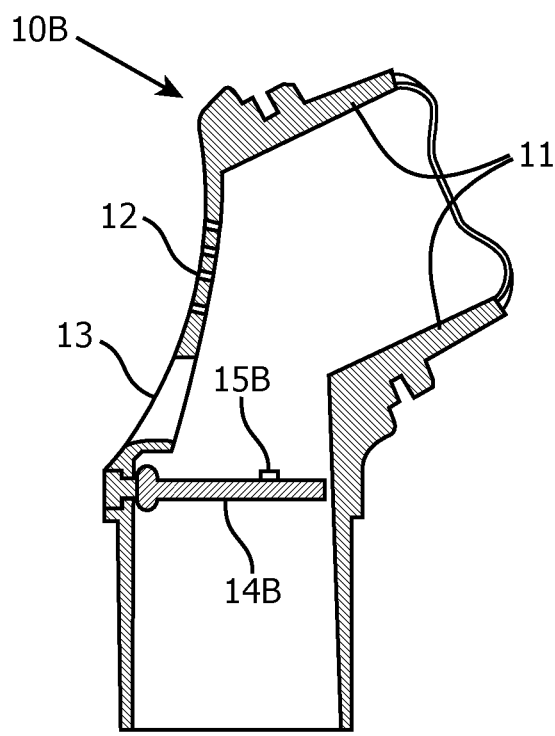
FIG. 8 is an side cross-sectional view and FIGS. 9 and 10 are bottom cross-sectional views of an elbow connector according to another exemplary embodiment of the invention.
Figures 9, 10:
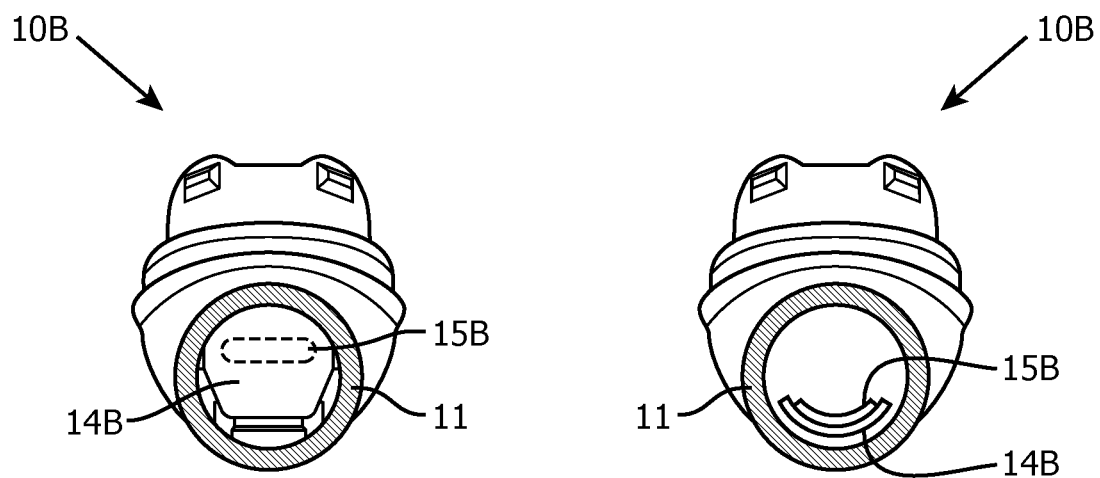

FIGS. 8-10 illustrate an elbow connector 10B including a valve member 14B having a ridge 15B formed on its top side in accordance with another exemplary embodiment of the disclosed concept. FIG. 8 is a side cross-sectional view of elbow connector 10B. FIG. 9 is a bottom cross-sectional view of elbow connector 10B when valve member 14B is in an unfolded position and FIG. 10 is a bottom cross-sectional view of elbow connector 10B when valve member 14B is folded down.

Elbow connector 10B is similar to elbow connector 10. However, the protrusion on valve member 14B of elbow connector 10B is a ridge 15B formed on the top side of valve member 14B rather than posts 15 formed on the bottom side of valve member 14. Ridge 15B provides structural support for valve member 14B. The structural support provided by ridge 15B helps to prevent valve member 14B from conforming to the shape of the interior of housing 11 when valve member 14B is in the folded down position, and thus helps to prevent valve member 14B from becoming stuck in the downward folded position.

In the exemplary embodiment shown in FIGS. 8-10, ridge 15B is a single ridge passing from the left to right sides of valve member 14B. However, it is contemplated that ridge 15B may take any suitable form that provides structural support to valve member 14B without departing from the scope of the disclosed concept. It is also contemplated that a textured pattern me be formed on the top side of valve member 14B may be used in place of ridge 15B without departing from the scope of the disclosed concept.

It is further contemplated that other mechanisms may be used in place of ridge 15B to provide structural support for valve member 14B. For example and without limitation, valve member 14B may be formed of an elastomeric material and a material having a higher durometer may be overmolded onto the elastomeric material to provide structural support for valve member 14B. Similarly, it is contemplated that an elastomeric material may be overmolded onto a stiffer material to form valve member 14B without departing from the scope of the disclosed concept.

Figure 11:
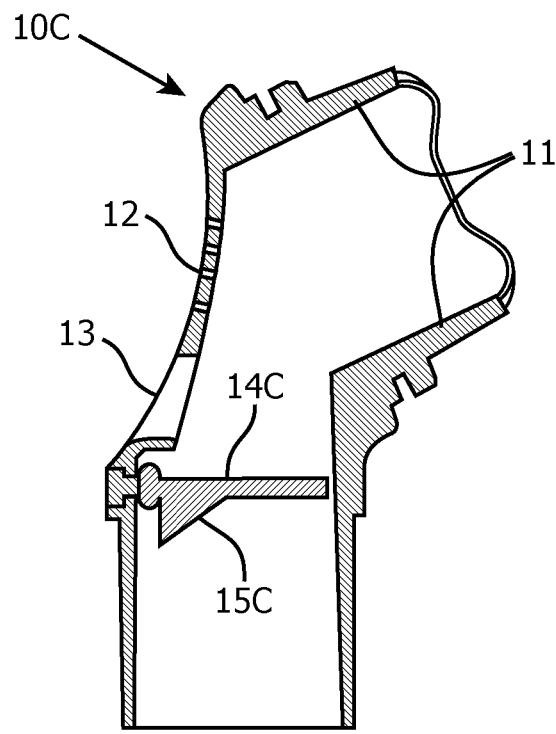
FIG. 11 is a side cross-sectional view and FIG. 12 is a bottom cross-sectional view of an elbow connector according to another exemplary embodiment of the invention.
Figure 12:
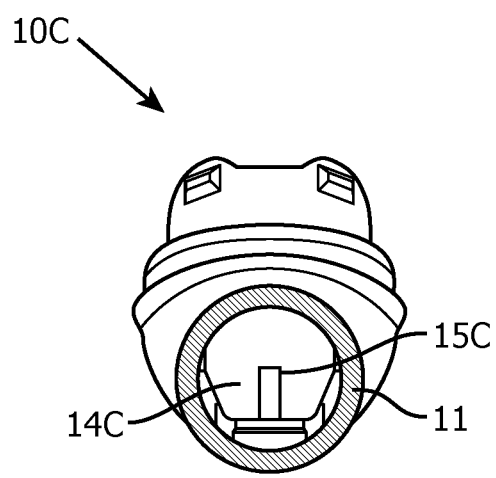

Referring now to FIGS. 11 and 12, an elbow connector 10C including a valve member 14C having a wedge 15C formed on its bottom side in accordance with another example embodiment of the disclosed concept is shown. FIG. 11 is a side cross-sectional view of elbow connector 10C and FIG. 12 is a bottom cross-sectional view of elbow connector 10C.

Elbow connector 10C is similar to elbow connector 10. However, the protrusion on valve member 14C of elbow connector 10C is a wedge 15C formed on the bottom side of valve member 14C rather than posts 15 formed on the bottom side of valve member 14. Wedge 15C is structured to abut against the interior of housing 11 in order to prevent valve member 14C from moving to the folded down position. Valve member 14C is still free to move to the folded up position such as when pressure is applied by air from the pressure generating device 4.

In the exemplary embodiment shown in FIGS. 11 and 12, wedge 15C is formed as a triangular shaped member on the bottom side of valve member 14C. However, it is contemplated that wedge 15C may have any suitable form which abuts against the interior of housing 11 to prevent valve member 14C from moving to the folded down position. For example and without limitation, wedge 15C may be replaced with a ridge that is tall enough to abut against the interior of housing 11 to prevent valve member 14C from moving to the folded down position. It is also contemplated that any number of wedges 15C may be formed on the bottom side of valve member 14C without departing from the scope of the disclosed concept.

Figure 13:
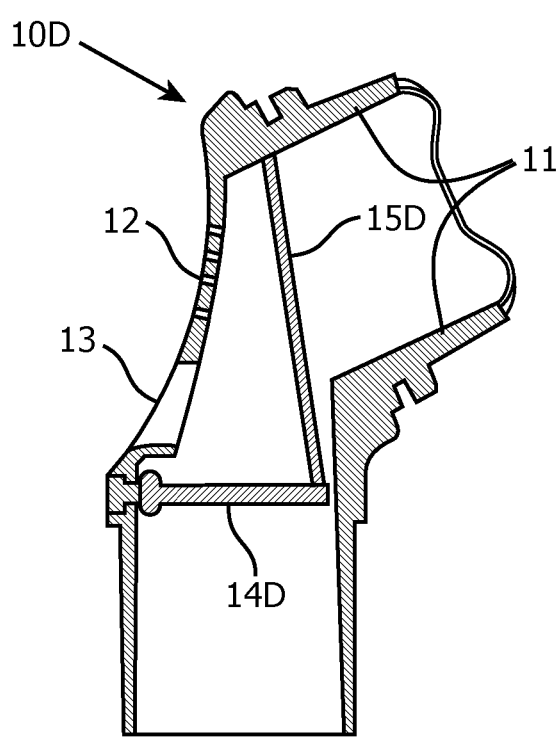
FIG. 13 is a side cross-sectional view of an elbow connector according to another exemplary embodiment of the invention.

Turning to FIG. 13, an elbow connector 10D including a valve member 14D having a tether 15D in accordance with yet another example embodiment of the disclosed concept is shown. FIG. 13 is a side cross-sectional view of elbow connector 10D.

Elbow connector 10D is similar to elbow connector 10. However, valve member 14D of elbow connector 10D has one end of a tether 15D attached thereto rather than having posts 15 formed thereon. The other end of tether 15D is attached to the interior of housing 11 at a point above valve member 14D. Tether 15D is structured to prevent valve member 14D from moving to the folded down position, but still allows valve member 14D to move to the folded up position.

Figure 14:
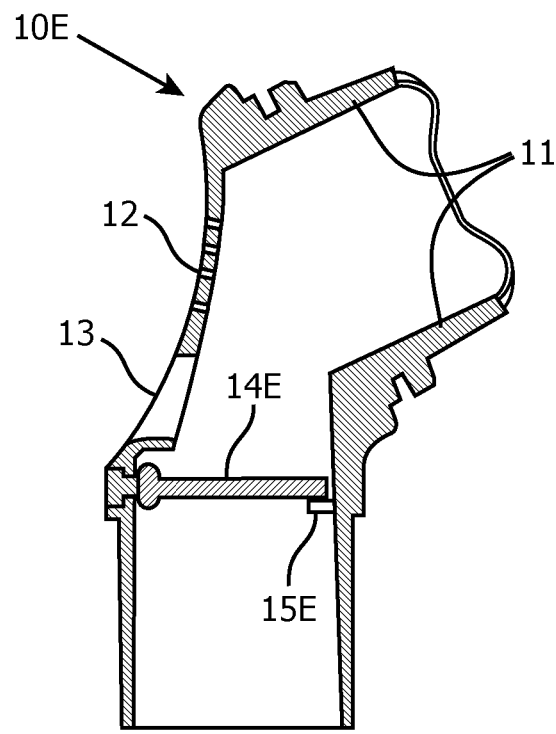
FIG. 14 is a side cross-sectional view and FIG. 15 is a bottom cross-sectional view of an elbow connector according to another exemplary embodiment of the invention.
Figure 15:
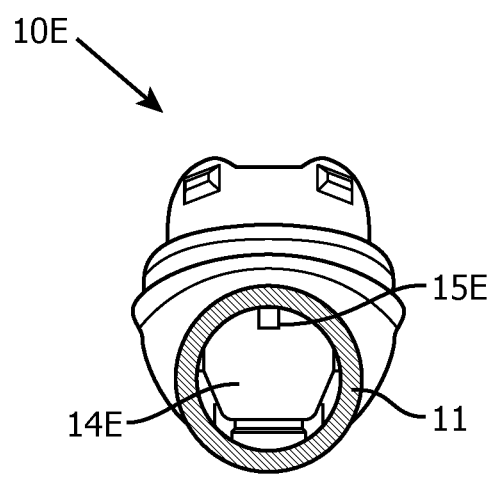

Referring now to FIGS. 14 and 15, an elbow connector 10E including a valve member 14E in accordance with yet another exemplary embodiment of the disclosed concept is shown. FIG. 14 is a side cross-sectional view of elbow connector 10E and FIG. 15 is a bottom cross-sectional view of elbow connector 10E.

Elbow connector 10E is similar to elbow connector 10. However, rather than having posts 15 formed on valve member 14 as in elbow connector 10, elbow connector 10E includes a post 15E formed on the interior surface of housing 11. Post 15E is structured to prevent valve member 14E from moving to the folded down position. Post 15E is formed on the interior surface of housing 11 opposite of the hinged end of valve member 14E. Post 15E prevents valve member 14E from moving to the folded down position while blocking a minimal area of the airflow path through elbow connector 10E.

While post 15E is formed on the interior of housing 11 in the exemplary embodiment shown in FIGS. 14 and 15, it is contemplated that any other protrusion suitable to prevent valve member 14E from moving to the folded down position may be formed on the interior of housing 11 without departing from the scope of the disclosed concept. For example and without limitation, it is contemplated that post 15E may be replaced with a ridge formed on the interior of housing 11 without departing from the scope of the disclosed concept. It is also contemplated that any number of posts 15E or other suitable protrusions may be formed on the interior of housing 11 without departing from the scope of the disclosed concept.

Figure 16:
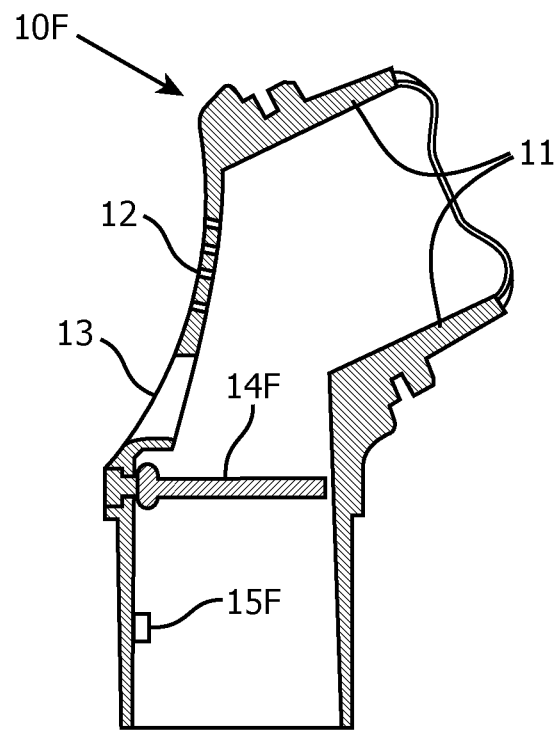
FIG. 16 is a side cross-sectional view and FIG. 17 is a bottom cross-sectional view of an elbow connector according to another exemplary embodiment of the invention.
Figure 17:
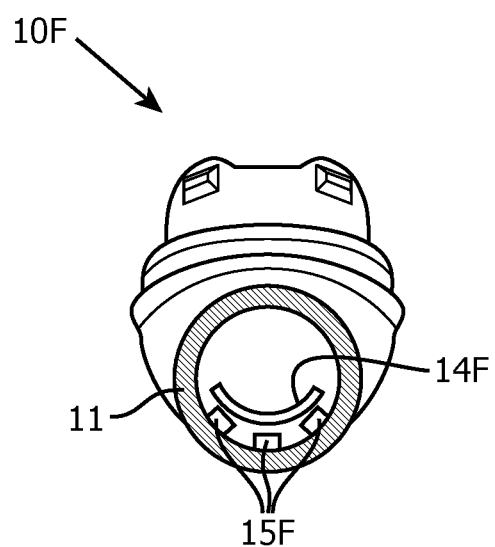

Referring now to FIGS. 16 and 17, an elbow connector 10F including a valve member 14F in accordance with yet another exemplary embodiment of the disclosed concept is shown. FIG. 16 is a side cross-sectional view of elbow connector 10F and FIG. 17 is a bottom cross-sectional view of elbow connector 10F.

Elbow connector 10F is similar to elbow connector 10. However, rather than having posts 15 formed on valve member 14 as in elbow connector 10, elbow connector 10F includes posts 15F formed on the interior surface of housing 11. Posts 15F are structured to abut against valve member 14F when valve member 14F is in the folded down position, as shown in FIG. 17. Posts 15F prevent valve member 14F from fully conforming to the interior shape of housing 11 when valve member 14F is in the downward folded position, and thus help to prevent valve member 14F from becoming stuck in the downward folded position.

While posts 15F are formed on the interior of housing 11 in the exemplary embodiment shown in FIGS. 16 and 17, it is contemplated that any other protrusion suitable to prevent valve member 14F from fully conforming to the interior shape of housing 11 when valve member 14F is in the downward folded position may be formed on the interior of housing 11 without departing from the scope of the disclosed concept. For example and without limitation, it is contemplated that posts 15F may be replaced with a ridge or pattern of ridges formed on the interior of housing 11 without departing from the scope of the disclosed concept. It is also contemplated that any number of posts 15F or other suitable protrusions may be formed on the interior of housing 11 without departing from the scope of the disclosed concept. Furthermore, it is contemplated that a textured pattern may be formed on the interior surface of housing 11 in place of posts 15F without departing from the scope of the disclosed concept.

Figure 18:
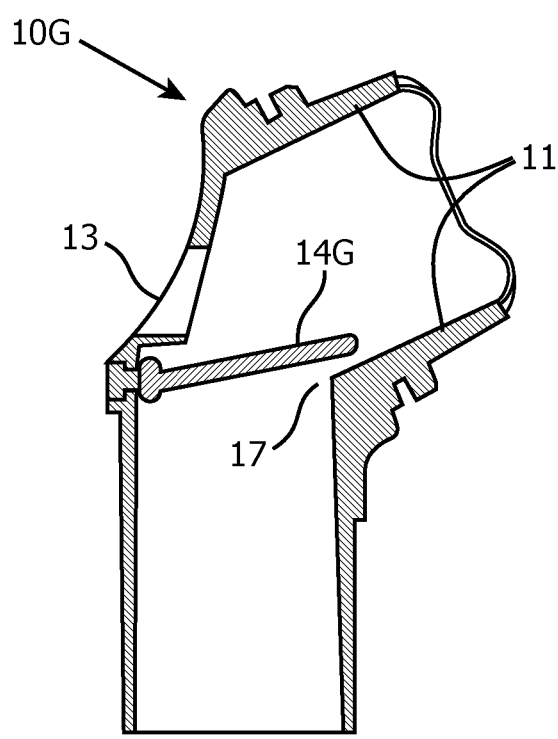
FIG. 18 is a side cross-sectional view of an elbow connector according to another exemplary embodiment of the invention.

Referring now to FIG. 18, an elbow connector 10G including a valve member 14G in accordance with another exemplary embodiment of the disclosed concept is shown. FIG. 18 is a side cross-sectional view of elbow connector 10G.

Elbow connector 10G is similar to elbow connector 10. However, in elbow connector 10G valve member 14G is located and sized so that it can extend over a bend 17 in elbow connector 10G. Bend 17 is the point at which the airflow path of elbow connector 10G changes direction. Valve member 14G is lengthened so that it extends over bend 17 and thus is prevented from moving to the downward folded position. Lengthening valve member 14G may cause valve member 14G to interfere with exhalation holes 12 when valve member 14G is in the folded up position. As such, exhalation holes (not shown in FIG. 18) may be relocated to a more suitable location.

While valve members have been described as being installed in elbow connectors, it will be understood that elbow connectors are just one type of fluid coupling member and any of the valve members described herein can also be installed in any other suitable fluid coupling member (e.g. without limitation, a delivery conduit) without departing from the scope of the disclosed concept.

While the present invention has been described in connection with a patient interface device used to treat, for example, OSA, it will be understood that that is meant to be exemplary, and that the principles of the present invention can be can also be applied in connection with other face masks applications where concern for asphyxia may occur, such as, without limitation, anesthesia delivery masks or general use face masks where users may be unable to manipulate a mask to maintain breathing. Furthermore, as the valve assembly embodiments described herein actuate upon very basic fluid dynamic principles, they may also be used in industrial applications, for example, and without limitation, as a combination check valve/bleed-off valve where air circulation may require access to atmosphere if direct system pressure is not applied. The target industrial applications would be smaller and low pressure air control systems like HVAC, furnace air control, or automotive relief systems.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A fluid coupling member, comprising:
    a housing having an interior and an exterior, the interior of the housing defining an airflow path through the fluid coupling member;
    a valve member being pivotally attached to the interior of the housing; and
    at least one protrusion formed on the valve member, wherein the at least one protrusion is structured to prevent the valve member from becoming stuck in a downward folded position against the housing, and wherein the at least one protrusion includes at least one of a post, a ridge, and a wedge, and
    wherein the valve member is structured to move between an unfolded position and the downward folded position, and
    wherein the downward folded position is a position in which the at least one protrusion formed on the valve member abuts against the interior of the housing.

2. The fluid coupling member of claim 1, wherein the at least one protrusion includes at least one post formed on a bottom side of the valve member.

3. The fluid coupling member of claim 2, wherein each post has a length that is greater than or equal to 1 mm.

4. The fluid coupling member of claim 2, wherein a ratio of a diameter of the airflow path through the coupling member to a length of each post is within a range of about 5.5 to 9.5.

5. The fluid coupling member of claim 1, wherein the at least one protrusion includes at least one ridge formed on the bottom side of the valve member.

6. The fluid coupling member of claim 1, wherein the at least one protrusion includes at least one ridge formed on a top side of the valve member.

7. The fluid coupling member of claim 6, wherein the at least one ridge includes a ridge passing from a left side to a right side of the valve member.

8. The fluid coupling member of claim 1, wherein the fluid coupling member is an elbow connector.

9. A patient interface device employing the fluid coupling member of claim 1.

10. A fluid coupling member, comprising:
    a housing having an interior and an exterior, the interior of the housing defining an airflow path through the fluid coupling member;
    a valve member being pivotally attached to the interior of the housing; and
    at least one protrusion formed on the valve member, wherein the at least one protrusion is structured to prevent the valve member from becoming stuck in a downward folded position against the housing, and wherein the at least one protrusion includes at least one of a post, a ridge, and a wedge, and
    wherein the at least one protrusion includes at least one ridge formed on the bottom side of the valve member, and
    wherein the at least one ridge is a crossing pair of ridges.

11. A fluid coupling member, comprising:
    a housing having an interior and an exterior, the interior of the housing defining an airflow path through the fluid coupling member;
    a valve member being pivotally attached to the interior of the housing; and
    at least one protrusion formed on the housing, wherein the at least one protrusion is structured to prevent the valve member from becoming stuck in a downward folded position against the housing,
    wherein the at least one protrusion is structured to abut against the valve member when the valve member is in the downward folded position,
    wherein the valve member is structured to move between an unfolded position and the downward folded position,
    wherein the unfolded position is a position in which the valve member is not folded up or down at a point where it is pivotally attached to the interior of the housing,
    wherein the downward folded position is a position in which the valve member is folded down at the point where it is pivotally attached to the interior of the housing, and
    wherein the housing is a unitary body.

12. The fluid coupling member of claim 11, wherein the at least one protrusion includes at least one post.

13. The fluid coupling member of claim 12, wherein the at least one post is a plurality of posts.

* * * * *